(12) United States Patent
Fries et al.

(10) Patent No.: US 8,822,933 B2
(45) Date of Patent: Sep. 2, 2014

(54) TIME-TO-DIGITAL CONVERTER FOR A MEDICAL IMAGING SYSTEM

(75) Inventors: Mark David Fries, Germantown, WI (US); James Widen, Sussex, WI (US); Paul Holtermann, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 124 days.

(21) Appl. No.: 13/529,532

(22) Filed: Jun. 21, 2012

(65) Prior Publication Data

US 2013/0341518 A1 Dec. 26, 2013

(51) Int. Cl.
*G01T 1/164* (2006.01)

(52) U.S. Cl.
USPC .................................................. 250/363.03

(58) Field of Classification Search
CPC .................................................... G04F 10/005
USPC ..................................... 250/363.03; 341/156
See application file for complete search history.

(56) References Cited

U.S. PATENT DOCUMENTS

| | | | |
|---|---|---|---|
| 6,593,575 B2 | 7/2003 | Fries | |
| 7,667,199 B2 | 2/2010 | Fries | |
| 2003/0201838 A1 | 10/2003 | Tam et al. | |
| 2004/0139276 A1 | 7/2004 | Srinivasan et al. | |
| 2006/0187226 A1 | 8/2006 | Bruno et al. | |
| 2011/0248874 A1* | 10/2011 | Cannillo et al. | 341/118 |
| 2012/0176159 A1* | 7/2012 | Webb et al. | 327/18 |

* cited by examiner

*Primary Examiner* — David Porta
*Assistant Examiner* — Edwin Gunberg
(74) *Attorney, Agent, or Firm* — Dean D. Small; The Small Patent Law Group (57) ABSTRACT

A timing circuit that includes a first serializer/deserializer (SERDES) configured to receive a parallel rate clock signal and a system clock start signal from an imaging system and generate a first output, a second SERDES configured to receive a stop signal that is based on an output from the medical imaging system and generate a second output, and a timestamp calculator configured to utilize the first and second outputs to generate a timestamp. A medical imaging system and a method of operating a timing circuit are also described.

19 Claims, 4 Drawing Sheets

TIME-TO-DIGITAL CONVERTER FOR A MEDICAL IMAGING SYSTEM

BACKGROUND OF THE INVENTION

The subject matter described herein relates generally to medical imaging systems, and more particularly, to a time-to-digital converter (TDC) utilized in a medical imaging system.

Radioactive tracers called "radiopharmaceuticals" are often used to perform medical imaging. As the radioactive tracer decays, the radioactive tracer emits positrons. The positrons travel a very short distance before they encounter an electron, and when this occurs, the positrons are annihilated and converted into two annihilation photons, or gamma rays. This annihilation is characterized by two features which are pertinent to positron emission tomography (PET) imaging systems. First, each gamma ray has an energy of 511 keV and second, two gamma rays are directed in nearly opposite directions. An image is generated by determining the number of such annihilations at each location within the field of view.

To generate the image, at least one known PET imaging system includes a detector ring assembly which converts the energy of each 511 keV photon into a flash of light (scintillation photons) that is sensed by a light sensor. Coincidence detection circuits connect to the detectors and record only those photons which are detected approximately simultaneously by detectors located on opposite sides of the patient, referred to as coincidence events.

To accurately determine coincidence events and thereby obtain useful information for generating the image, PET imaging systems utilize timing circuits to accurately identify and log the times at which photons are received at the detectors. The timing circuits typically include digital counters and digital counter latches that receive both the count signals from the digital counters and impulse signals from the detector whenever photons are detected. Based upon the count signals, the counter latches effectively time-stamp the impulse signals with times indicative of when the impulse signals are received, and output this information for use by the PET imaging system in determining coincidence events. However, known timing circuits, including the digital counters, are relatively complex and may result in an increase in cost to fabricate.

SUMMARY OF INVENTION

In one embodiment, a timing circuit is provided. The timing circuit includes a first serializer/deserializer (SERDES) configured to receive a parallel rate clock signal and a system clock start signal from an imaging system and generate a first output, a second SERDES configured to receive a stop signal that is based on an output from the medical imaging system and a parallel rate clock signal, generates a second output, and a timestamp calculator configured to utilize the first and second outputs to generate a timestamp. A medical imaging system and a method of operating a timing circuit are also described.

In another embodiment, a method of operating an imaging system that includes a field programmable gate array is provided. The method includes receiving at a first serializer/deserializer (SERDES) receive circuit a parallel-rate clock and a time-to-digital (TDC) start signal and generating a first parallel word that represents a leading edge position of the TDC start signal using the first SERDES receive circuit, receiving at a second SERDES receive circuit the parallel-rate clock and a TDC stop signal and generating a second parallel word that represents a leading edge position of the TDC stop signal using the second SERDES receive circuit, receiving the parallel-rate clock and the TDC start signal at a first leading edge detection circuit and generating a TDC start edge found signal and an encoded value representing a first non-zero or a first zero bit position in the TDC start signal, receiving the parallel-rate clock and the TDC stop signal at a second leading edge detection circuit and generating and generating a TDC stop edge found signal and an encoded value representing a first non-zero or a first zero bit position in the TDC stop signal, receiving the parallel-rate clock, the TDC start edge found signal, and the TDC stop edge-found signal at a first binary counter circuit and generating a binary count representing a number of parallel-rate clock cycles that have elapsed since the a TDC start signal was activated to generate a TDC start signal conversion, receiving the parallel-rate clock, the TDC stop edge found signal at a second binary counter circuit and generating a binary count representing a number of parallel-rate clock cycles that have elapsed since the a TDC stop signal was activated to generate a TDC stop signal conversion, and subtracting the TDC stop signal conversion from the TDC start signal conversion to generate a timestamp.

In a further embodiment, an imaging system is provided. The imaging system includes a plurality of detectors supported by a gantry, a plurality of acquisition circuits coupled to the detectors, wherein the acquisition circuits provide event detection signals, and a field programmable gate array (FPGA) utilized to timestamp the event detection signals. The field programmable gate array is programmed to include a first serializer/deserializer (SERDES) configured to receive a parallel rate clock signal and a system clock start signal from an imaging system and generate a first output, a second SERDES configured to receive a stop signal that is based on an output from the medical imaging system and generate a second output, and a timestamp calculator configured to utilize the first and second outputs to generate a timestamp.

DETAILED DESCRIPTION

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for time-stamping signals received from an imaging system. The time-stamping may be performed using a timing circuit that includes a pair of serializer/deserializer (SERDES) devices. In operation, the timing circuit is configured to determine a time difference between, for example, a start signal and a stop signal, that are input to the timing circuit. In various embodiments, the SERDES devices are implemented as programmable gate arrays which are highly configurable as described in more detail below. In operation, one SERDES, and associated devices, is utilized to identify a timing value for the start signal and a second SERDES, and associated devices, is utilized to identify a timing value for the stop signal. The first and second timing values are then utilized to generate the timestamp.

Figure 1:
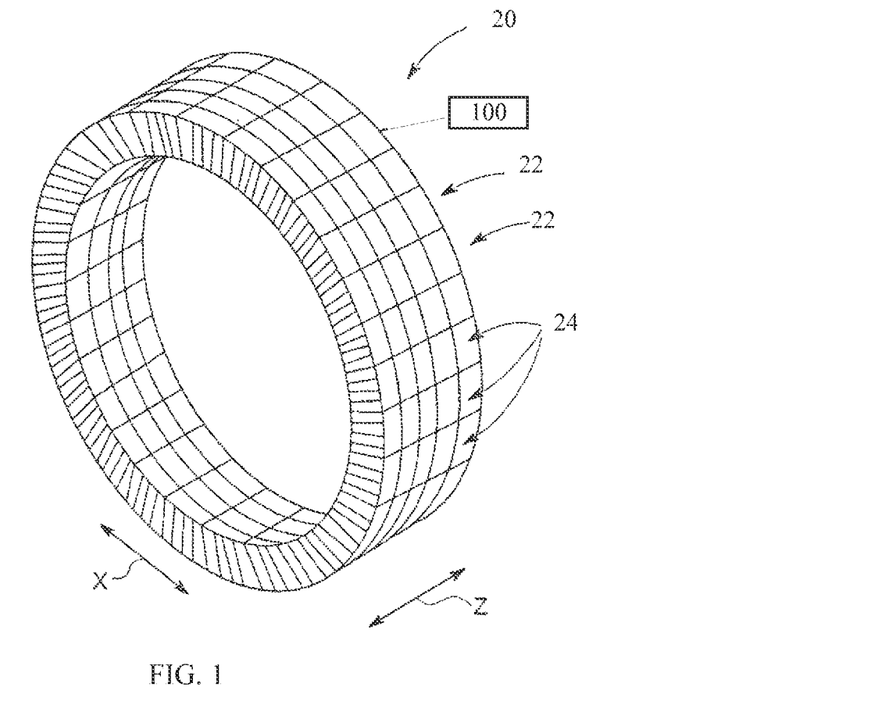
FIG. 1 is a perspective view of a positron emission tomography (PET) detector assembly in accordance with an embodiment.

Various embodiments may be used in combination with gamma ray detectors (also referred to herein as gamma detectors) in a positron emission tomography (PET) system having a PET detector assembly 20 shown in perspective view in FIG. 1. However, it should be appreciated that the gamma detectors and various embodiments may be implemented in different types of imaging and non-imaging systems. In the illustrated embodiment, the PET detector assembly 20 is coupled to a timing circuit (or assembly) that includes electronics for processing received signals and time-stamping the received signals. The timestamped signals generated by the timing circuit may be utilized to identify coincidence pairs which are subsequently utilized to generate an image as is described in more detail below. Thus, the PET detector assembly 20 may be utilized to provide signals to a timing circuit 100.

In various embodiments, the PET detector assembly 20 includes a plurality of detector modules 22 that are arranged in a ring to form the PET detector assembly 20. Each detector module 22 is assembled from a plurality of detector units 24. Thus, a plurality of detector units 24 is assembled to form a single detector module 22, and a plurality of detector modules 22 is assembled to form the PET detector assembly 20. In one embodiment, the PET detector assembly 20 includes twenty-eight detector modules 22 that are coupled together such that the PET detector assembly 20 has a ring shape. In some embodiments, each detector module 22 includes twenty detector units 24 that are arranged in a 4×5 matrix. It should be realized that the quantity of detector modules 22 utilized to form the PET detector assembly 20 is exemplary, and that the PET detector assembly 20 may have more than or fewer than twenty-eight detector modules 22. Moreover, it should be realized that quantity of detector units 24 utilized to form each detector module 22 is exemplary, and that the detector module 22 may have more than or fewer than twenty detector units 24.

Figure 2:
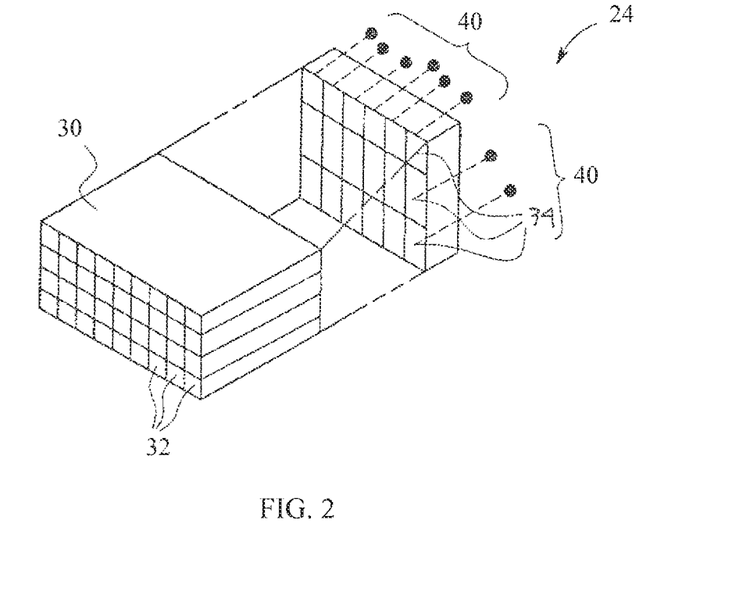
FIG. 2 is a perspective view of a detector unit formed in accordance with an embodiment.

FIG. 2 is a perspective view of an exemplary detector unit 24 that may form a portion of the detector module 22 shown in FIG. 1. In various embodiments, the detector unit 24 includes a scintillator block 30 having one or more scintillator crystals 32 that are arranged along an x-axis and a z-axis. In one embodiment, the scintillator block 30 has thirty-six crystals 32 that are arranged in a 4×9 matrix. However, it should be realized that the scintillator block 30 may have fewer than or more than thirty-six crystals 32, and that the crystals 32 may be arranged in a matrix of any suitable size. It also should be noted that the scintillator crystals 32 may be formed from any suitable material such as bismuth germinate (BGO), Cerium-doped Lutetium Yttrium Orthosilicate (LYSO) or Gadolinium Oxyorthosilicate (GSO), among others.

The detector unit 24 also includes a plurality of light sensors 34, illustrated as a plurality of photosensors, which may be any suitable photo-detectors that sense or detect light or other electromagnetic energy. In the illustrated embodiment, the light sensors 34 are Silicon Photomultipliers (SIPMs). The plurality of light sensors 34 are coupled at an end of the scintillator block 30 opposite a detector face 38. It should be noted that in some embodiments, such as to form a Depth-of-Interaction (DOI) detector, a reflector or reflective material may be provided on the detector face end.

In various embodiments, the detector unit 24 has eighteen light sensors 34 on each end of the scintillator block 30 that are arranged in a 3×6 matrix. However, it should be realized that the detector unit 24 may have fewer than or more than eighteen light sensors 34 and that the light sensors 34 may be arranged in a matrix of any suitable size. For example, some embodiments include 36, 54 or 100 crystals 32 having corresponding light sensors 34 that are arranged in a 6×6 matrix, 9×6 matrix or 10×10 matrix, respectively. It should be noted that in various embodiments, a one-to-one coupling between the light sensor 34 (e.g., a photosensor) and the crystal 32 is not provided, such that there is a one-to-multiple coupling between the light sensor 34 and the crystal 32. However, in other embodiments, a one-to-one coupling between the light sensor 34 (e.g., a photosensor) and the crystal 32 may be provided. Also, the light sensors 34 may have a different size or shape. In some embodiments, the light sensors 34 are larger than 3×3 mm$^2$. However, in other embodiments, larger or smaller light sensors 34 may be used, such as 4×6 mm$^2$ light sensors 34.

In one embodiment, the light sensors 34 are avalanche photodiodes that are connected in parallel and operated above a breakdown voltage in a Geiger mode. For example, the light sensors 34 may be SIPMs in various embodiments that are configured as single photon sensitive devices formed from an avalanche photodiode array on a silicon substrate. However, it should be noted that the light sensors 34 may be any type of light sensor, for example, any type of photosensor.

In operation, the scintillator crystals 32 convert the energy, deposited by a gamma ray impinging on the scintillator crystal 32, into visible (or near-UV) light photons. The photons are then converted to electrical analog signals by the light sensors 34. More specifically, when a gamma ray impinges on any one of the scintillators 32 in a detector unit 24, the scintillator detecting the gamma ray converts the energy of the gamma ray into visible light that is detected by the light sensors 34 in the detector unit 24. Thus, in the exemplary embodiment, each detector unit 24 is configured to output "n" analog signals 40.

Figure 3:
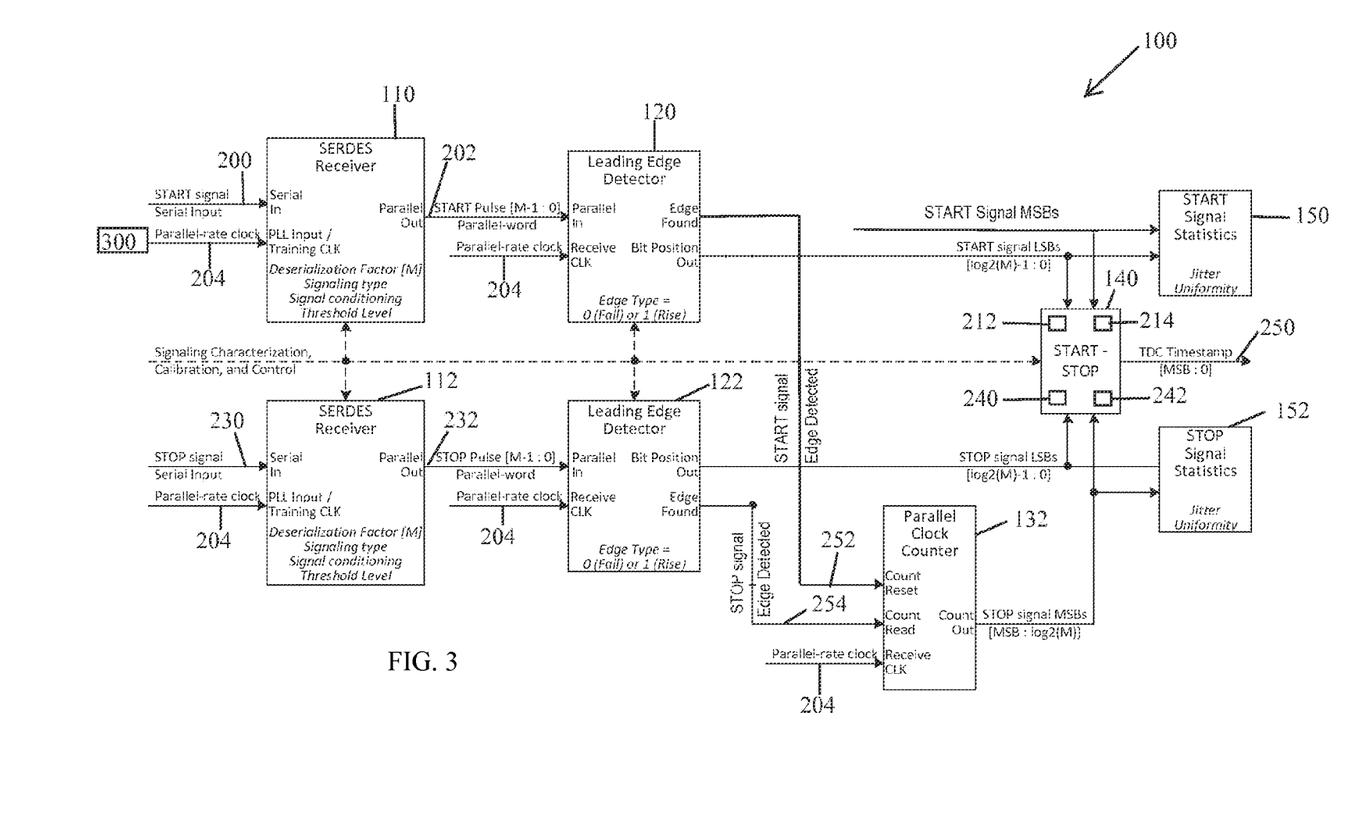
FIG. 3 is schematic illustration of a time-to-digital (TDC) converter formed in accordance with various embodiments.

FIG. 3 is schematic diagram of the timing circuit 100 shown in FIG. 1. In various embodiments, the timing circuit 100 is implemented as a time-to-digital converter (TDC 100). In the illustrated embodiment, the TDC 100 includes a first SERDES receiver 110, a second SERDES receiver 112, a first leading edge detector 120, a second leading edge detector 122, a parallel clock counter 132, a timestamp calculator 140, a start signal jitter detection device 150, and a stop signal uniformity detection device 152. Each of these circuits 110, 112, 120, 122, 132, 140, 150, and 152 may be implemented on a field programmable gate array (FPGA), a microcircuit, or other electronic device, such as an ASIC.

In various embodiments, the SERDES receiver 110 is configured to receive a serial input data stream, such as a start signal 200, and output a parallel word, e.g. an output wherein all the bits are output in a parallel stream having a predetermined width, such as a start pulse 202, that represents a leading edge position of the start signal 200. Thus, in the illustrated embodiment, the SERDES receiver 110 is configured as a single input/parallel output (SIPO) device.

In operation, the start signal 200 is utilized to reset the timestamper on a parallel-rate clock 204. Accordingly, the start signal 200 may also be referred to herein as a reset major, a reset clock, or a system clock. In the illustrated embodiment, the SERDES receiver 110 is further configured to receive the parallel-rate clock signal 204. In various embodiments, the clock signal 204 may be generated using, for example, a programmable parallel-rate clock, such as a parallel-rate clock 300 shown in FIG. 4. In various embodiments, the clock 300 may be implemented as a single-phase clock that includes a phase locked loop (PLL) circuit 302 that is capable of providing clock signals at a plurality of frequencies. More specifically, the single-phase clock 300 is configurable and/or reprogrammable by the operator such that the period of the single-phase clock may be changed to a wide variety of frequencies. Moreover, it should be realized that the clock 300 may be replicated to generate additional clocks.

Figure 4:
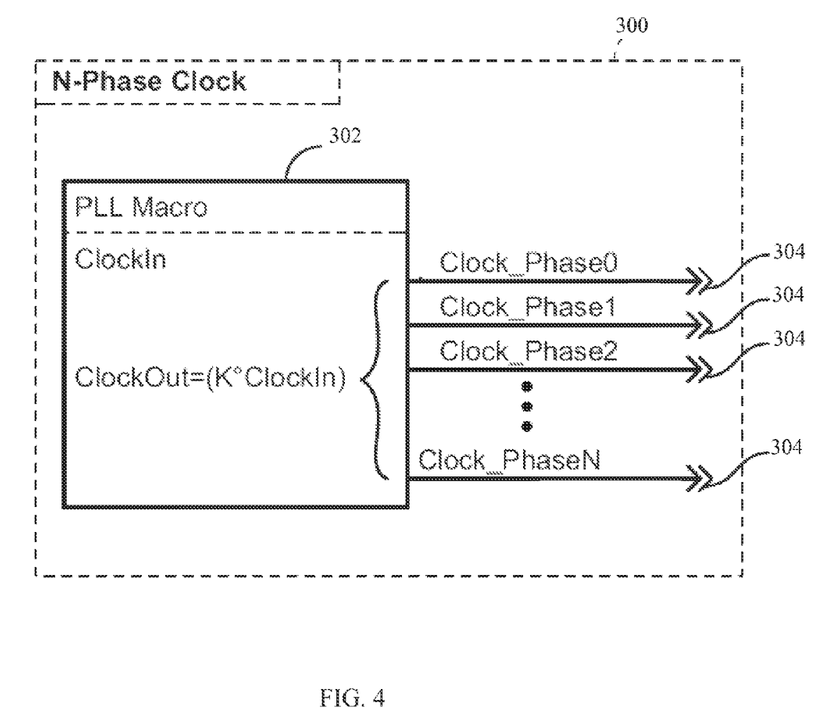
FIG. 4 is a schematic illustration of an exemplary clock formed in accordance with various embodiments.

In operation, the phase locked loop circuit 302 is reconfigurable to generate, for example, N variable-frequency clock signals, where N is limited only by the number of clocks that the PLL can generate. Each clock signal generated is set by the PLL to be 360/N degrees out of phase with a nearest neighbor clock signal. Given that each phase of the clock 300 operates at F-MHz, the PLL macro 302 generates a clock that operates at (F*N)-MHz. For example, as shown in FIG. 4, the PLL circuit 302 is shown as generating four clock signals 304 wherein each clock signal 304 is ninety degrees out of phases with a nearest neighbor clock signal 304. As a further example, if N is set by the operator to equal eight, i.e. N=8, the PLL circuit 302 will generate eight clock signal 304 wherein each clock signal 304 is forty-five degrees out of phase with a nearest neighbor clock signal 304. The N-phase clock signals 304 generated by the clock 300 are in turn provided to the SERDES receiver 110. Moreover, the N-phase clock signals 304 generated by the clock 300 are also provided to the second SERDES receiver 112, the first leading edge detector 12, the second leading edge detector 122, and the parallel clock counter 132.

In operation, both edges of the N-phase clock 300 may be utilized during time-stamping, thereby creating the 2N-phase clock. Each clock signal generated is set by the PLL to be 360/(2*N) degrees out of phase with a nearest neighbor clock signal. Given that each phase of the clock 300 operates at F-MHz, the PLL macro 302 generates a clock that operates at (F*N*2)-MHz. Both edges of the N-phase clock signals 304 generated by the clock 300 are in turn provided to the SERDES receiver 110. Moreover, both edges of the N-phase clock signal 304 generated by the clock 300 are also provided to the second SERDES receiver 112, the first leading edge detector 120, the second leading edge detector 122, and the parallel clock counter 132.

Referring again to FIG. 2, in operation the parallel-rate clock signal 304 functions as a division of the serial rate clock, e.g. the start signal 200. The SERDES receiver 110 is configured to utilize a deserialization factor (M), to modify or change the least significant bit (LSB) size and the timestamp. More specifically, the parallel rate clock signal and the deserialization factor (M) may be utilized to change the number of times the SERDES receiver 110 computes time.

For example, assume that a single-phase clock signal 304 is utilized as the parallel-clock rate 204 input to the SERDES receiver 110 and is set to 10-nanoseconds (ns) and assume that the deserialization factor (M) within the SERDES is set to 10. Accordingly, the TDC 100 functions as a timestamper with a 1-ns LSB. Additionally, assume that a single-phase clock signal 304 is utilized as the parallel-clock rate 204 and is set to 10-ns and assume that the deserialization factor (M) is set to 20. Accordingly, the TDC 100 functions as a timestamper with a 500-picosecond (ps) LSB. Accordingly, in operation, a single-phase clock signal 304, input to the parallel rate clock signal 204, is utilized to set the speed of the TDC 100. Moreover, it should be realized that the parallel clock rate signal 204 may be replicated, by utilizing an N-phase clock signal 304, such that multiple parallel-clock rate signals 204 are input to the SERDES receiver 110. For example, assume that a 4-phase clock signal 304 is the parallel-clock rate signal 204 and is set to 10-ns and assume that the deserialization factor (M) is set to 20. Accordingly, the TDC 100 would operate as a timestamper with a 125-ps LSB. Thus, in operation, the parallel-clock rate signal 204 and the deserialization factor (M) may be adjustable to increase and/or decrease the time-stamping capability of the TDC 100 and therefore increase and/or decrease the resolution of the TDC 100.

In various embodiments, the SERDES receiver 110 functions as a shift register, which in the illustrated embodiment, is implemented as a FPGA or an ASIC. In operation, because the SERDES receiver 110 is implemented as a FPGA or ASIC, the SERDES receiver 110 has improved capabilities. For example, the SERDES receiver 110 is configurable to adjust the clock frequency as described above. Moreover, the SERDES receiver 110 is configurable to match a signal type input to the TDC 100. The SERDES receiver 110 may condition the start signal to remove or filter poor quality start signals. Moreover, the SERDES receiver 110 may have a configurable threshold level, e.g. where the SERDES receiver 110 identifies 1's and 0's in the start signal 200. Accordingly, the SERDES receiver 110 is configurable to enable the SERDES receiver 110 to perform multiple operations not previously enabled using a conventional timing circuit. More specifically, the SERDES receiver 110 functions as a SIPO shift register that may be configured to operate at any number of clock frequencies, may count any number of bits, and may accept any type of signaling at the front end. Accordingly, the SERDES receiver 110 may be utilized with any timestamper, such as for example, the TDC 100 shown in FIG. 3.

The operation of the TDC 100 is now explained with reference to the start signal 200. In various embodiments, the output from the SERDES receiver 110, e.g. the start pulse word 202, is a parallel-word that is sized based on the deserialization factor (M). For example, assume that the deserialization factor (M) is 20, then for every set of 20 bits input to the SERDES receiver 110, the SERDES receiver 110 outputs a parallel word that is 20 bits wide. It should be realized that the deserialization factor (M) may be set to any value.

The start pulse 202 is then input to the leading edge detector 120 along with the parallel-rate clock signal 204. In operation, the leading edge detector 120 is configured to generate a start signal LSB value 212 for the start signal 200. More specifically, the leading edge detector 120 is configured to, for example, examine the start pulse 202 and identify a transition from 0 to 1 (for active low-to-high signals) position or a transition from 1 to 0 (for active high-to-low) position within the serial start pulse parallel word 202. The position of the transition from 0 to 1 or from 1 to 0, relative to the complementary bits in the start pulse 202, is decoded into the start signal LSB value 212 for the start signal 200.

For example, assume that the parallel-clock rate 204 input to the SERDES receiver 110 is set to 10-ns and assume that the deserialization factor (M) is 10. Accordingly, every 1-ns, a bit from the start signal 200 moves through the shift register, i.e. the SERDES receiver 110. Moreover, the SERDES receiver 110 outputs a 10 bit word every 10-ns, i.e. the start pulse word 202. Somewhere in at least one of the 10 bit words, e.g. the start pulse words 202, is a transition of bits, from 0 to 1, which indicates when the start signal 200 went active or a transition of bits, from 1 to 0, when the start signal 200 went inactive. It should be realized that each start pulse word 202 may not have a LSB that is, for example, a 1. Accordingly, the leading edge detector 120 is configured to analyze multiple start pulse words 202 to identify the start signal LSB value 212 for start signal 200. For example, assume that the SERDES receiver 110 outputs five start pulses 202. Moreover, assume that the first four start pulse words 202 are all 0's. Moreover, assume that the third digit in the fifth start pulse word 202 is identified as a transition from 0 to 1. Accordingly, the leading edge detector 120 outputs a start signal LSB value 212 of "3" indicating that the LSB of the start pulse 202 is the third digit in the word being analyzed. In various embodiments, the start signal LSB value 212 for the start signal 200 is input to the timestamp calculator 140 and the start signal jitter detection device 150 and processed as described herein.

After the leading edge detector 120 identifies the start signal LSB value 212 for the start signal 200, the start pulse MSB value 214 for the start value is assumed to be equal to "0", since the start signal represents the system clock and will have only a minimal delay from the system clock signal. It should therefore be realized that the start pulse MSB value 214 of "0" and the start pulse LSB value 212 of "3" are combined to form a timestamp of "03" of the start signal 200.

The operation of the TDC 100 is now explained with reference to the STOP signal. In various embodiments, the SERDES receiver 112 is configured to receive serial input data stream, e.g. a stop signal 230 and output a parallel word, e.g. the stop pulse word 232 that represents a leading edge position of the stop signal 230. Thus, in the illustrated embodiment, the SERDES receiver 112 is configured as a SIPO device. In various embodiments, the stop signal 230 is a serial stream of data acquired from a medical imaging system, such as the PET detector assembly 20 shown in FIGS. 1 and 2. However, it should be realized that the TDC 100 may be utilized to timestamp and/or determine a time difference between any signals input to the TDC 100, and that the stream of data acquired from the PET detector assembly 20 is one such signal. Accordingly, in the illustrated embodiment, the stop signal 230 represents the "n" analog signals 40 shown in FIG. 2. In various embodiments, the stop signal 230 may also be referred to herein as a trigger pulse.

As described above, the SERDES receiver 112 is also configured to receive the clock signal at the input 204. In operation, the SERDES 112 is also configured to utilize a deserialization factor (M), to modify or change the LSB size and the timestamp. More specifically, the parallel rate clock signal and the deserialization factor (M) may be utilized to change the number of times the SERDES receiver 112 computes time as described above with respect to the SERDES receiver 110. Accordingly, in various embodiments, the SERDES receiver 112 functions similarly to the SERDES receiver 110 to output a stop pulse word 232 which is a parallel-word that is sized based on the deserialization factor (M). The stop pulse word 232 is then input to the leading edge detector 122 along with the parallel-rate clock signal 204. In operation, the leading edge detector 122 is configured to generate the LSB of the timestamp for the stop signal 230.

More specifically, the leading edge detector 122 is configured to, for example, examine the stop pulse word 232 and identify the first non-zero (for active low-to-high signals) or first non-one (for active high-to-low) position within the serial stop pulse word 232. The first non-zero or non-one bit position, relative to the complementary bits in the stop pulse word 232, is decoded into the a stop signal LSB value 240 for stop signal 230.

After the leading edge detector 122 identifies the stop signal LSB value 240 for the stop signal 230, a count read signal 254 is transmitted to the parallel clock counter 132. In operation, the parallel clock counter 132 is configured to determine which word, e.g. stop pulse word 232, was identified as including the stop pulse LSB bit. More specifically, as described above, assume that the parallel clock counter 132 receives a stop pulse word 232 every 10-ns via the count read channel. Moreover, as described above, assume that the SERDES receiver 112 outputs five stop pulse words 232. Moreover, assume that the first four stop pulse words 232 are all 0's. Moreover, assume that the third digit in the fifth stop pulse word 232 is identified as a transition from 0 to 1. Accordingly, the parallel clock counter 132 is configured to count the quantity of stop pulse words 232 between the start pulse and the stop pulse LSB bits being identified. In the example described, the parallel clock counter 132 counts five stop pulse words 232, wherein the fifth stop pulse word 232 includes the stop pulse LSB bit as identified by the count reset signal 252 generated by the leading edge detector 120. Accordingly, in the illustrated embodiment, the parallel clock counter 132 is configured to output a stop pulse most significant bit (MSB) 242 of "5" indicating that the fifth word, e.g. the fifth stop pulse word 232 was identified as having the stop pulse LSB. It should therefore be realized that the stop pulse MSB value 242 of "5" and the stop pulse LSB value 240 of "3" are combined to form a timestamp of "53" of the stop signal 230. In various embodiments, the start pulse MSB 242 is also input to the timestamp calculator 140 and the stop signal uniformity statistics device 152 and processed as described herein.

In operation, the timestamp calculator 140 is configured to generate a timestamp value 250 that is applied to the signals 230 received at the SERDES receiver 112. In the exemplary embodiment for example, assume that the start signal LSB value 212 is 3, the start signal MSB value 214 is 5, the stop signal LSB value 240 is 7, and the stop signal MSB value 242 is 2. Accordingly, the timestamp value 250 would be 26, e.g. 53–27.

In operation, the jitter detection device 150 is configured to provide statistics for jitter or skew in the start signal 200. More specifically, in operation the start signal 200 may vary over time or may have an intrinsic skew. For example, assume that the start signal 200 is set to timestamp at 200-ns increments. However, in some instances, the start signal 200 may timestamp at for example, 199.9-ns during one conversion or 200.1-ns during another conversion. Accordingly, the jitter detection device 150 is configured to monitor the start signal 200 to determine if the start signal 200 is time-stamping at the set value. In various embodiments, if the start signal 200 is not time-stamping at the set value, the jitter detection device 150 is configured to modify or adjust the start signal to timestamp at the set value as described herein. Moreover, the jitter detection device 150 may be configured to determine if the start signal 200 has a consistent skew, from some arbitrary time reference. For example, assume that the start signal 200 is set to timestamp with O-ns skew, from some arbitrary time reference. However in some instances, the start signal 200 may consistently timestamp with for example, 0.1-ns skew during every conversion. Accordingly, the jitter detection device 150 is configured to monitor the start signal 200 to determine if the start signal 200 is time-stamping at the set value. In various embodiments, if the start signal 200 is time-stamping with values with consistent skews, the jitter detection device 150 is configured to modify or calibrate the start signal 200 to timestamp at the set value as described herein.

Similarly, the uniformity detection device 152 is configured to monitor the stop signal 230. Because, the stop signal 230, in various embodiments, is generated based on the signals 40, the timestamp MSB's 242 and the timestamp LSB's 240 of the stop signal 230 should be relatively random. Accordingly, in various embodiments, the uniformity detection device 152 is configured to monitor the stop signal 230, using for example, a histogram of a plurality of stop signals 230, to determine if an event was recorded at every timestamp in the 200-ns time period.

Described herein are methods and systems for time-stamping a signal. In various embodiments, the apparatus is implemented as a TDC which uses SERDES communication circuitry. The deserializer function of the communications circuit is used to locate, in time, the transition of an input signal. More specifically, the TDC is configured to determine the time difference between a start signal and a stop signal. Both the start and stop signals are captured by serial inputs to the deserializer part of the SERDES communication circuit. The SERDES communication circuitry is robust and may be implemented in a programmable gate arrays. Setup and hold times to inputs of the SERDES communication circuitry may be in the 1-2 ps range, and inputs may be hardened against going metastable. Thus, the SERDES communication circuitry is highly configurable.

In operation, to form the LSB of the timestamp, the parallel output of the deserializer circuit is examined and the 0 to 1 transition (for active low-to-high signals) position or 1 to 0 transition (for active high-to-low) position within the serial stream is determined. The 0 to 1 transition or 1 to 0 transition position, relative to the complementary bits in the parallel word, is decoded into the LSB's in the timestamp of the start and stop signals. The timestamp for the stop signal is arithmetically subtracted from the timestamp of the start signal, to determine the TDC conversion.

To form the MSB's of the timestamp, the number of parallel-signal-rate clock transitions elapsed since the start signal made an active low-to-high (or high-to-low) transition, are counted. This count, captured when the stop signal makes an active low-to-high (or high-to-low) transition, is used to determine the MSB's of the start-to-stop TDC conversion. These MSB's are combined with the LSB's previously described, to determine the complete timestamp.

The input deserialization rate determines the LSB precision of the TDC function. For example, a smaller LSB size may be achieved by running the input deserialization rate at a higher value. In this manner, the LSB size is programmable, within the limits of the device used to implement the method. In various embodiments, a course TDC timestamp of 833-ps is implemented with a 1.2-giga-bit-per-second (Gb) deserialization rate. In various other embodiments, a finer TDC timestamp of 500-ps is implemented with a 2.0-Gb deserialization rate.

In addition, for an even higher precision TDC, both the start and stop signals may be input to multiple SERDES circuits, with each SERDES circuit having a stepped phase as a clock input. Accordingly, if N SERDES inputs are utilized for the conversion, this effectively increases the precision of the TDC by a factor of N, the number of clock phases. In one example, if the SERDES clock has a baud rate of 5.0-Gb, the TDC precision would be 200-ps. By using four SERDES inputs, and a four-phase SERDES clock, the TDC precision would be increased to 50-ps.

In addition, the electrical signaling standard, for the start and stop input signals, is programmable within the limits of the device used to implement the methods. Signaling may be either single-ended, with transistor-transistor logic (TTL) or complementary-symmetry metal-oxide-semiconductor (CMOS) voltage-mode signaling, or signaling may be differential, with Low-voltage differential signaling (LVDS), Low-voltage positive emitter-coupled logic (LVPECL), or current mode logic (CML) current-mode signaling. In one embodiment, an 833-ps TDC timestamp is captured with a differential LVDS input circuit. In another embodiment, a 500-ps TDC timestamp is captured with a differential CML input circuit.

In addition, the electrical signaling input characteristics for the start and stop input signals, are programmable, within the limits of the device used to implement the method. Signal input threshold levels and receive equalization levels are programmable to match the output characteristics of the device driving the start and stop signals, as well as the transmission line characteristics of the respective signal paths.

Moreover, if multiple TDC functions are implemented in a single programmable gate array, by using a greater number of resources, more than one stop signal may be timestamped in a single device. Additionally, a calibration may be performed to determine and remove skew, due to electronic differences between the start and stop signal inputs. For example, in one embodiment, if the start signal is multiplexed into both the start and stop inputs to the device, followed by a TDC conversion, the result is the skew between the start and stop signals. This calibration result may be stored and applied as a correction to all subsequent TDC conversions. In various embodiments, the calibration may be performed automatically at device power-up. In other embodiments, the calibration may be performed upon request.

In addition, because the TDC function is part of a programmable gate array, statistics about the function can be captured in real time. For example, in various embodiments, the cycle-to-cycle jitter of the start signal, which is an important factor in the quality of the TDC timestamp, may be measured by capturing successive conversions of the start signal, subtracting one from another, and accumulating a histogram of the results. The statistical distribution of the histogram represents the jitter in the start signal. In other embodiments, successive conversions of the stop signal may be accumulated in a histogram; and the histogram may be analyzed for statistics such as uniformity and missing TDC codes.

Figure 5:
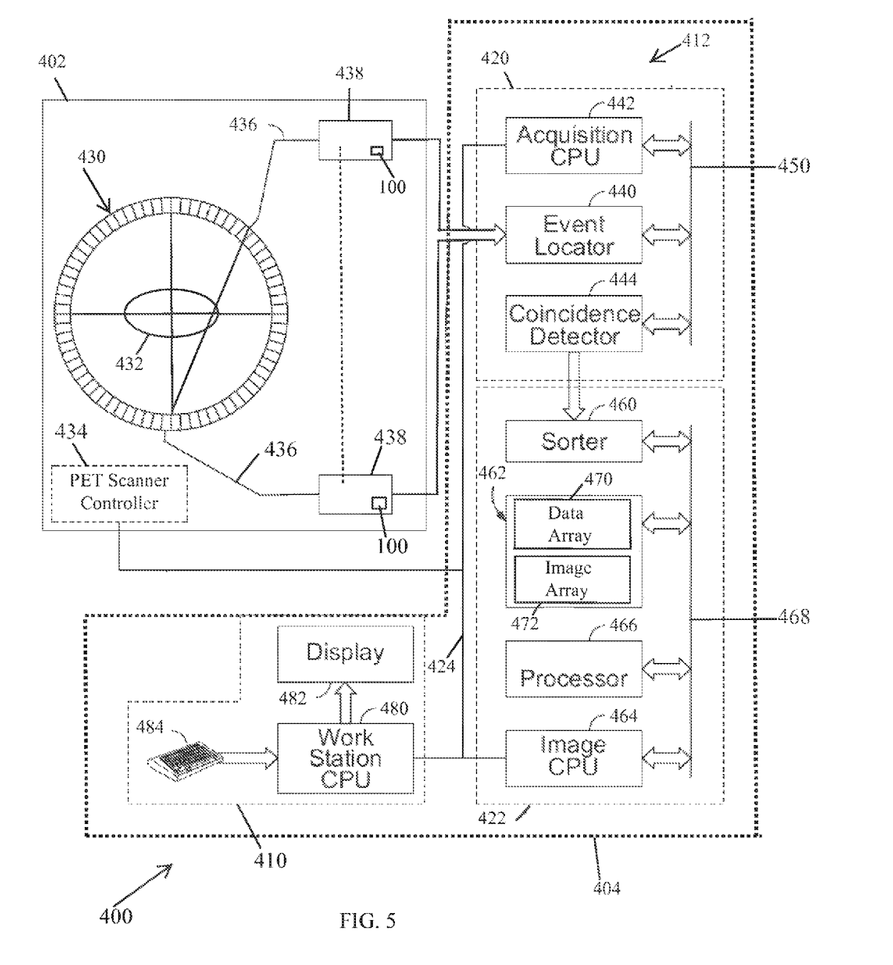
FIG. 5 is a diagram of a PET system formed in accordance with various embodiments.

FIG. 5 is a block diagram of an exemplary embodiment of a PET system 400 in which various embodiments of the invention may be implemented. The PET system 400 includes a PET scanner 402 and a controller 404 to control image reconstruction processes. The controller 404 is also configured to recover timing information based as described in more detail above and may be embodied as the PET timing circuit (shown in FIG. 1). The controller 404 includes an operator workstation 410 and a processor 412. The processor 412 includes a data acquisition processor 420 and an image reconstruction processor 422. The PET scanner 402, the operator workstation 410, the data acquisition processor 420 and the image reconstruction processor 422 are interconnected via a communication link 424 (e.g., a serial communication or wireless link). The PET scanner 402, which typically includes a gantry (not shown), acquires scan data and transmits the data to the data acquisition processor 420. The operation of the PET scanner 402 is controlled from the operator workstation 410. The data acquired by the data acquisition processor 420 is reconstructed using image reconstruction processor 422.

The PET scanner 402 may operate, using, for example, a plurality of detector rings. One such detector ring, the detector ring 430, is illustrated in FIG. 10, which may be embodied as the PET detector assembly 20 (shown in FIG. 1). The detector ring 430 includes a central opening, in which an object 432 (e.g., a patient) may be positioned, using, for example, a motorized table that is aligned with the central axis of the ring 430. The motorized table moves the object 432 into the central opening of detector the ring 430, in response to one or more commands received from the operator workstation 410. A PET scanner controller 434, also referred to as a gantry controller, is provided (e.g., mounted) in the PET scanner 402. The PET scanner controller 434 responds to the commands received from the operator workstation 410 through the communication link 424. Therefore, the operation of the PET scanner 402 is controlled from the operator workstation 410 through the PET scanner controller 434.

The detector ring 430 includes a plurality of detector elements for performing a PET scan of the object 432. For example, there may be 420 crystals per ring and 24 rings in the scanner. When a photon collides with a crystal on the detector, the photon produces a scintilla on the crystal. Each photosensor produces an analog signal on a communication line 436 when a scintillation event occurs. A set of acquisition circuits 438 is provided within the PET scanner 402 to receive these analog signals. The acquisition circuits 438 produce digital signals indicating the location and total energy of the event. The acquisition circuits 438 also produce an event detection pulse that indicates the time at which the scintillation event was detected. In various embodiments, the event detection pulses are timestamped using the TDC 100 shown in FIG. 1. These timestamped digital signals are then transmitted through a communication link, for example, a cable, to an event locator circuit 440 in the data acquisition processor 420.

The data acquisition processor 420 includes the event locator 440, an acquisition CPU 442, and a coincidence detector 444. The data acquisition processor 420 periodically samples the signals produced by the acquisition circuits 438. The acquisition CPU 442 controls communications on a back-plane bus 450 and on the communication link 424. The event locator circuit 440 processes the information pertaining to each valid event and provides a set of digital numbers or values indicative of the detected event. For example, this information indicates when the event occurred, as determined by the TDC 100, and the identity of the scintillation crystal that detected the event. An event data packet is communicated to the coincidence detector 444 through the back-plane bus 450. The coincidence detector 444 receives the event data packets from the event locator circuit 440 and determines if any two of the detected events are in coincidence. In this context, the coincidence is determined by a number of factors. First, the time markers in each event data packet must be within a predetermined time period, for example, 6-ns, of each other. Secondly, the LOR formed by a straight line joining the two detectors that detect the coincidence event should pass through the field of view in PET scanner 402. Events that cannot be paired are discarded. Coincident event pairs are recorded as a coincidence data packet that is communicated through a communication link to a sorter 460 in the image reconstruction processor 422.

The image reconstruction processor 422 includes the sorter 460, a memory module 462, an image CPU 464, an array processor 466, and a back-plane bus 468. The sorter 460 counts all events that occur along each projection ray and organizes them into a coincidence data set. In one embodiment, this data set is organized as a data array 470, referred to as a sinogram. The data array 470 is stored in the memory module 462. The back-plane bus 468 is linked to the communication link 424 through the image CPU 464, which controls communication through the back-plane bus 468. The array processor 466 is also connected to the back-plane bus 468, receives the data array 470 as an input, and reconstructs images in the form of the image arrays 462. The resulting image arrays 472 are stored in the memory module 462.

The images stored in the image array 472 are communicated by the image CPU 464 to the operator workstation 410. The operator workstation 410 includes a CPU 480, a display device 482, and an input device 484. The CPU 480 connects to the communication link 424 and receives inputs (e.g., user commands) from the input device 484, which may be, for example, a keyboard, mouse, or a touch-screen panel. The operator can control the calibration of the PET scanner 402, the configuration of the PET scanner 402, and the positioning of the object 432 for a scan through the input device 484 and associated control panel switches. Similarly, the operator can also control the display of the resulting image on the display device 482 and perform image-enhancement functions, using programs executed by the workstation CPU 480.

The processor 412 is configured to process the scan data received from the detector elements. The scan data includes, for example, sinogram and timing information that is received by processor 412 from the detector elements during an imaging scan. The timing information in one embodiment is the difference in time at which two photons emitted in an annihilation event are detected by detector elements. The timing information may include timestamp information relating to a measured photon event detected by a pair of detector elements. The timestamp information is the time at which each photon is detected by a detector element, which in various embodiments include two times for each detector, namely the time the interaction was detected by each of the pair of light sensors 34 (shown in FIG. 2). Further, the processor 412 is configured to process the energy and timing data, as described in more detail herein. The energy and timing information may be used to perform timing recovery as described herein.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A timing circuit comprising:
   a first serializer/deserializer (SERDES) configured to receive a parallel rate clock signal and a system clock start signal from an imaging system and generate a first output based on the system clock start signal;
   a second SERDES configured to receive the parallel rate clock signal and a stop signal that is based on an output from the imaging system and generate a second output based on the output from the imaging system; and
   a timestamp calculator configured to compare the first output from the first SERDES based on the system clock signal and the second output from the second SERDES based on the output from the medical imaging system to generate a timestamp.

2. The timing circuit of claim 1, further comprising:
   a first leading edge detector configured to receive the first output and determine at least one least significant bit of the system clock start signal; and
   a second leading edge detector configured to receive the second output and determine at least one least significant bit of the stop signal.

3. The timing circuit of claim 2, further comprising a parallel clock counter configured to determine at least one most significant bit of the stop signal, the timestamp calculator configured to utilize the least significant bits of the system clock start signal, the least significant bits of the stop signal, and the most significant bits of the stop signal to generate the timestamp, wherein the timestamp is generated by subtracting a first value from a second value, the first value including the most significant bits of the stop signal and the least significant bits of the stop signal, the second value including the most significant bits of the start signal and the least significant bits of the start signal.

4. The timing circuit of claim 1, wherein the first SERDES and the second SERDES comprises single input parallel output shift registers programmed on a field programmable gate array.

5. The timing circuit of claim 1, wherein the imaging system includes a positron emission tomography (PET) detector assembly, the timestamp indicating a time that a gamma ray is detected at the PET detector assembly, the stop signal corresponding to a triggering signal corresponding to the detection of the gamma ray at the PET detector assembly.

6. A method of operating an imaging system that includes a field programmable gate array, said method comprising:
   receiving at a first serializer/deserializer (SERDES) receive circuit a parallel-rate clock and a time-to-digital (TDC) start signal, and generating a first parallel word that represents a leading edge position of the TDC start signal using the first SERDES receive circuit;
   receiving at a second SERDES receive circuit the parallel-rate clock and a TDC stop signal and generating a second parallel word that represents a leading edge position of the TDC stop signal using the second SERDES receive circuit, the TDC stop signal based on an output of the imaging system;
   receiving the parallel-rate clock and the TDC start signal at a first leading edge detection circuit and generating a TDC start edge found signal and an encoded value representing a 0 to 1 transition or 1 to 0 transition bit position in the TDC start signal;

receiving the parallel-rate clock and the TDC stop signal at a second leading edge detection circuit and generating a TDC stop edge found signal and an encoded value representing a 0 to 1 transition or 1 to 0 transition bit position in the TDC stop signal;

receiving the parallel-rate clock and the TDC start edge found signal at a first binary counter circuit, and generating a binary count representing a number of parallel-rate clock cycles between the TDC start signal and the TDC start edge found signal to generate a TDC start signal conversion;

receiving the parallel-rate clock and the TDC stop edge found signal at a second binary counter circuit and generating a binary count representing a number of parallel-rate clock cycles between the TDC stop signal and the TDC stop edge found signal to generate a TDC stop signal conversion; and subtracting the TDC stop signal conversion from the TDC start signal conversion to generate a timestamp.

7. The method of claim 6, wherein a plurality of TDC stop conversion circuits are selected and an electronic skew between the TDC stop conversion circuits is measured during a calibration and a correction is applied during subsequent TDC stop signal conversions.

8. The method of claim 6, wherein the parallel-rate input clock's frequency is re-configurable during operation and the frequency is selected to scale the precision of TDC conversion.

9. The method of claim 6, wherein a SERDES circuit serial-to-parallel deserialization factor is re-configurable during operation and the deserialization factor is selected to scale the precision of the TDC conversion.

10. The method of claim 6, wherein a SERDES circuit electronic input type is selectable, and the SERDES circuit electronic input type is selected to match an electronic output type of a circuit generating the TDC start signal and the TDC stop signal.

11. The method of claim 6, wherein a SERDES circuit electronic input threshold level is selectable or re-configurable during operation and the threshold level is selected to match an electronic output level of a circuit generating the TDC start signal and the TDC stop signal.

12. The method of claim 6, wherein a SERDES circuit electronic input signal conditioning is selectable during design or re-configurable during operation and is selected to match an electronic output signal of a circuit generating the TDC start signal and the TDC stop signal.

13. The method of claim 6, wherein the parallel-rate input clock is divided into N-phases, where each clock is 360/N out-of-phase with a nearest neighbor clock.

14. The method of claim 13, wherein the SERDES receive circuits, the leading-edge detection circuits, and the binary counter circuits are duplicated for each of the N-phases of the parallel-rate input clock.

15. The method of claim 14, wherein for each phase of the parallel-rate clock, there is a corresponding TDC start conversion and stop conversion, with each conversion circuit receiving a single, unique phase of the parallel-rate clock.

16. An imaging system comprising:
a plurality of detectors supported by a gantry;
a plurality of acquisition circuits coupled to the detectors, wherein the acquisition circuits provide event detection signals; and
a field programmable gate array (FPGA) utilized to timestamp the event detection signals, said field programmable gate array programmed to include:
a first serializer/deserializer (SERDES) configured to receive a parallel rate clock signal and a system clock start signal from the imaging system and generate a first output based on the system clock start signal;
a second SERDES configured to receive the parallel rate clock signal and a stop signal that is based on an output from the imaging system and generate a second output based on the output from the imaging system; and
a timestamp calculator configured to compare the first output from the first SERDES based on the system clock signal and the second output from the second SERDES based on the output from the medical imaging system to generate a timestamp.

17. The imaging system of claim 16, wherein the FPGA further comprises:
a first leading edge detector configured to receive the first output and determine at least one least significant bit of the system clock start signal; and
a second leading edge detector configured to receive the second output and determine at least one least significant bit of the stop signal.

18. The imaging system of claim 16, wherein the FPGA further comprises a parallel clock counter configured to determine at least one most significant bits of the stop signal, the timestamp calculator configured to utilize the least significant bits of the system clock start signal, the least significant bits of the stop signal, the most significant bits of the system clock start signal, and the most significant bits of the stop signal to generate the timestamp, wherein the timestamp is generated by subtracting a first value from a second value, the first value including the most significant bits of the stop signal and the least significant bits of the stop signal, the second value including the most significant bits of the start signal and the least significant bits of the start signal.

19. The imaging system of claim 16, wherein the imaging system includes a positron emission tomography (PET) detector assembly, the timestamp indicating a time that a gamma ray is detected at the PET detector assembly, the stop signal corresponding to a triggering signal corresponding to the detection of the gamma ray at the PET detector assembly.

* * * * *